(12) United States Patent
Perrett et al.

(10) Patent No.: US 8,784,884 B2
(45) Date of Patent: Jul. 22, 2014

(54) PANCREATIC ENZYME COMPOSITIONS AND METHODS FOR TREATING PANCREATITIS AND PANCREATIC INSUFFICIENCY

(76) Inventors: Stephen Perrett, Princeton, NJ (US); Ruth Thieroff-Ekerdt, Mendham, NJ (US); Gopi Venkatesh, Vandalia, OH (US); Konstantinos Efthymiopoulos, Trelex (CH)

(*) Notice: Subject to any disclaimer, the term of this patent is extended or adjusted under 35 U.S.C. 154(b) by 633 days.

(21) Appl. No.: 12/568,064

(22) Filed: Sep. 28, 2009

(65) Prior Publication Data

US 2011/0064799 A1 Mar. 17, 2011

Related U.S. Application Data

(60) Provisional application No. 61/243,467, filed on Sep. 17, 2009.

(51) Int. Cl.
| | |
|---|---|
| *A61K 9/48* | (2006.01) |
| *A61K 9/14* | (2006.01) |
| *A61K 38/43* | (2006.01) |
| *A61K 38/54* | (2006.01) |
| *A61P 1/18* | (2006.01) |

(52) U.S. Cl.
USPC .......... 424/452; 424/490; 424/94.1; 424/94.2

(58) Field of Classification Search
USPC ................... 424/452, 490, 94.1, 94.2
See application file for complete search history.

(56) References Cited

U.S. PATENT DOCUMENTS

| | | | |
|---|---|---|---|
| 4,447,412 A | 5/1984 | Bilton | |
| 8,071,089 B2 | 12/2011 | Schuler et al. | |
| 2004/0121010 A1* | 6/2004 | Hirsh et al. | 424/468 |
| 2006/0121017 A1 | 6/2006 | Margolin et al. | |
| 2009/0117180 A1 | 5/2009 | Ortenzi et al. | |
| 2009/0148545 A1* | 6/2009 | Falk et al. | 424/757 |

FOREIGN PATENT DOCUMENTS

WO   WO 2008/102264 A2 *   8/2008   ............... A61K 9/48

OTHER PUBLICATIONS

Young, PCT International Search Report and Written Opinion for International Application No. PCT/US2010/049203, mailed Oct. 22, 2010.

\* cited by examiner

*Primary Examiner* — Ernst Arnold
*Assistant Examiner* — Hong Yu

(57) ABSTRACT

Compositions of the present invention, comprising the combination of enterically coated and uncoated pancreatic enzyme-containing beads are useful for treating or preventing pancreatitis pain, and optionally disorders associated with digestive enzyme deficiencies.

23 Claims, No Drawings

PANCREATIC ENZYME COMPOSITIONS AND METHODS FOR TREATING PANCREATITIS AND PANCREATIC INSUFFICIENCY

CROSS REFERENCE TO RELATED APPLICATIONS

This application claims priority to U.S. Provisional Appl. No. 61/243,467, filed Sep. 17, 2009, the entire contents of which are herein incorporated by reference in their entirety for all purposes.

BACKGROUND OF THE INVENTION

In cases of pancreatic insufficiency, pancrelipase and other pancreatic enzymes products (PEPs) can be administered to at least partially remedy the enzyme deficiency caused by various diseases affecting the pancreas, such as pancreatitis, pancreatectomy, cystic fibrosis, etc. The use of pancreatic enzymes in the treatment of pancreatic insufficiency is an essential part of the therapy of patients afflicted with cystic fibrosis. Without these supplements, patients become severely nutritionally impaired. This nutritional impairment can be life threatening if left untreated, particularly in the case of infants.

In addition to nutritional impairment (e.g., fat malabsorption, etc.) the majority of patients suffering from chronic pancreatitis also experience severe and often debilitating pain associated with the condition. The cause of pancreatic pain is uncertain, but has been hypothesized to be caused by pancreatic hyperstimulation as a result of the loss of feedback regulation of CCK releasing peptide. Normally, the release of pancreatic protease in response to the ingestion of a meal results in the degradation of CCK releasing peptide present in the upper GI tract, which causes a decrease in pancreatic contraction and enzyme secretion once sufficient digestive enzymes have been produced for digestion. For patients suffering from pancreatic insufficiency, the CCK releasing peptide is insufficiently degraded, thus allowing continued (hyper) stimulation of the pancreas. Although not wishing to be bound by any particular theory, according to this hypothesis for pain generation, the administration of protease enzymes (e.g. in pancreatic enzyme formulations) should degrade the CCK releasing peptide, thereby ameliorating pancreatic hyperstimulation and the resulting pancreatic pain.

Pancreatic enzymes show optimal activity under near neutral and slightly alkaline conditions. Under gastric conditions, lipase enzymes, which are often present in therapeutic enzyme compositions, are expected to become increasingly and irreversibly inactivated with decreasing pH and/or an increasing duration of exposure to low pH conditions, resulting in a loss of biological activity. Accordingly, exogenously administered enzymes are generally protected against gastric inactivation, e.g., with enteric coatings, so as to remain intact and protected from gastric acids during their transit through the stomach and into the duodenum. However, since CCK releasing peptide is secreted high in the GI tract, conventional enterically coated pancreatic enzyme preparations may not release protease enzymes sufficiently quickly or in the appropriate part of the GI tract to sufficiently degrade CCK releasing peptide and thereby reduce or eliminate pancreatic pain.

Uncoated enzyme preparations would not present the problem of slow or incomplete release in the GI tract, but would be expected to become substantially inactivated in the low pH environment of the stomach, and thus not provide sufficient levels of active digestive enzyme to treat the nutritional impairment caused by pancreatic insufficiency. One approach to treating pancreatic pain with uncoated enzyme preparations is to co-administer uncoated enzyme with proton pump inhibitors in an attempt to decrease enzyme degradation in the stomach so that some active enzyme, in particular lipase, may survive into the duodenum (Lieb et al., Aliment. Pharmacol. Ther. 29, 706-719 (2009)). Alternatively, pancreatic pain has been treated with relatively high doses of coated or uncoated pancreatic enzyme to ensure that sufficient active enzyme was delivered to the duodenum (Winstead et al., Pancreatology 9, 344-350 (2009)). For example, uncoated enzyme preparations dosed at 64,000 units of lipase, and having a nominal protease activity of 240,000 units (per meal) are suggested for the relief of pancreatic pain (Lieb et al.).

Based on a number of small clinical studies in which uncoated enzymes appeared to perform better the coated enzyme preparations used in other studies (Lieb et al.), the conventional wisdom is that coated enzyme preparations are not recommended for the treatment of pancreatic pain, while uncoated enzyme preparations may be suitable. To-date, however, there has been no controlled clinical trial that has adequately demonstrated the efficacy of pancreatic enzymes, coated or uncoated, in the treatment of pain associated with pancreatitis.

However, in order to treat both pancreatic pain (e.g. with uncoated enzyme preparations) and nutritional impairment (e.g. with coated enzyme preparations), conventional treatment methods suggest that very high doses of enzyme would be required: i.e., about 4 enterically-coated pancreatin pills, and 4 uncoated pancreatin pills per meal. This is based on the mid-point of the recommended mid-dosing of CREON 24, and expert recommendations for the dosing of uncoated enzymes (Winstead et al.), as there is presently no approved uncoated product for the treatment of pain. This places a very considerable burden on the patient and means that the total dose of enzymes that are given to a patient may give rise to safety concerns (Smyth et al. Fibrosing colonopathy in cystic fibrosis: results of a case-control study. *Lancet.* 1995; 346: 1247-1251; FitzSimmons et al. High-dose pancreatic-enzyme supplements and fibrosing colonopathy in children with cystic fibrosis. *New England Journal of Medicine.* 1997; 336: 1283-1289).

The present inventors have surprisingly found that a single dosage faun comprising the combination of a relatively lower amount of enterically coated digestive enzyme with uncoated digestive enzyme provides effective treatment of pancreatic pain and effective control of nutritional impairment, for example fat malabsorption. In addition, the present inventors have surprisingly found that a very low dose of enterically coated enzymes is effective in the treatment of malabsorption due to pancreatic insufficiency, e.g. in patients suffering from chronic pancreatitis.

SUMMARY OF THE INVENTION

In one embodiment, the present invention is directed to a multi-particulate digestive enzyme composition comprising enterically coated digestive enzyme-containing beads, and uncoated digestive enzyme-containing beads, wherein the enterically coated digestive enzyme-containing beads comprise a core and an enteric coating disposed over the core, wherein the core comprises a therapeutically effective amount of digestive enzymes, and the enteric coating comprises an enteric polymer; and the uncoated digestive enzyme-containing beads comprise a therapeutically effective amount of digestive enzymes, and is substantially free of an enteric polymer coating.

In another embodiment, the present invention is directed to a method of treating pancreatitis pain, comprising administering a composition of the present invention to a patient in need thereof.

In still another embodiment, the present invention is directed to a method of treating pancreatic exocrine insufficiency, comprising administering to a patient in need thereof a therapeutically effective dose of an enterically coated digestive enzyme, wherein said dose ranges from about 100 to about 300 USP lipase units/kg/meal.

DETAILED DESCRIPTION OF THE INVENTION

One aspect of the present invention is directed to a stabilized digestive enzyme composition comprising a combination of enterically coated and uncoated digestive enzyme-containing beads. The term "stabilized digestive enzyme" means a digestive enzyme which maintains substantial enzymatic activity after long-term storage. The term "digestive enzyme" denotes an enzyme in the alimentary tract which breaks down the components of food so that they can be taken or absorbed by the organism.

Non-limiting classes of digestive enzymes suitable for use in the present invention include lipases, amylases and proteases. Non-limiting examples of digestive enzymes include pancrelipase (also referred to as pancreatin), lipase, co-lipase, trypsin, chymotrypsin, chymotrypsin B, pancreatopeptidase, carboxypeptidase A, carboxypeptidase B, glycerol ester hydrolase, phospholipase, sterol ester hydrolase, elastase, kininogenase, ribonuclease, deoxyribonuclease, α-amylase, papain, chymopapain, glutenase, bromelain, ficin, β-amylase, cellulase, β-Galactosidase, lactase, sucrase, isomaltase, and mixtures thereof.

In one embodiment of the present invention, the stabilized digestive enzyme is a pancreatic enzyme. The term "pancreatic enzyme" as used herein refers to any one of the enzyme types present in the pancreatic secretion, such as amylase, lipase, protease, or mixtures thereof, or any extractive of pancreatic origin having enzymatic activity, such as pancreatin. The pancreatic enzyme can be obtained through extraction from the pancreas, produced artificially, or obtained from sources other than the pancreas, such as from microbes, plants or other animal tissues.

In another embodiment of the present invention, the stabilized digestive enzyme is pancrelipase. The terms "pancrelipase" or "pancreatin" denote a mixture of several types of enzymes, including amylase, lipase, and protease enzymes. Pancrelipase is commercially available, for example from Nordmark Arzneimittel GmbH, or Scientific Protein Laboratories LLC.

In one embodiment of the compositions of the present invention, the stabilized digestive enzyme comprises a lipase. The term "lipase" refers to an enzyme that catalyzes the hydrolysis of lipids to glycerol and simple fatty acids.

Examples of lipases suitable for the present invention include, but are not limited to animal lipase (e.g., porcine lipase), bacterial lipase (e.g., *Pseudomonas* lipase and/or *Burkholderia* lipase), fungal lipase, plant lipase, recombinant lipase (e.g., produced via recombinant DNA technology by a suitable host cell, selected from any one of bacteria, yeast, fungi, plant, insect or mammalian host cells in culture, or recombinant lipases which include an amino acid sequence that is homologous or substantially identical to a naturally occurring sequence, lipases encoded by a nucleic acid that is homologous or substantially identical to a naturally occurring lipase-encoding nucleic acid, etc.), chemically-modified lipase, or mixtures thereof.

In another embodiment of the compositions of the present invention, the stabilized digestive enzyme comprises an amylase. The term "amylase" refers to glycoside hydrolase enzymes that break down starch, for example α-amylases, β-amylases, γ-amylases, acid α-glucosidases, salivary amylases such as ptyalin, etc.

The amylases suitable for use in the compositions of the present invention include, but are not limited to animal amylases, bacterial amylases, fungal amylases (e.g., *Aspergillus*™ amylase and, preferably, is *Aspergillus oryzae* amylase), plant amylases, recombinant amylases (e.g., produced via recombinant DNA technology by a suitable host cell, selected from any one of bacteria, yeast, fungi, plant, insect or mammalian host cells in culture, or recombinant amylases which include an amino acid sequence that is homologous or substantially identical to a naturally occurring sequence, amylases encoded by a nucleic acid that is homologous or substantially identical to a naturally occurring amylase-encoding nucleic acid, etc.), chemically modified amylases, or mixtures thereof.

In another embodiment of the compositions of the present invention, the stabilized digestive enzyme comprises a protease. The term "protease" refers generally to enzymes (e.g., proteinases, peptidases, or proteolytic enzymes) that break peptide bonds between amino acids of proteins. Proteases are generally identified by their catalytic type, e.g., aspartic acid peptidases, cysteine (thiol) peptidases, metallopeptidases, serine peptidases, threonine peptidases, alkaline or semi-alkaline proteases, neutral and peptidases of unknown catalytic mechanism.

Non-limiting examples of proteases suitable for use in the compositions or oral dosage forms of the present invention include serine proteases, threonine proteases, cysteine proteases, aspartic acid proteases (e.g., plasmepsin) metalloproteases, glutamic acid proteases, etc. in addition, proteases suitable for use in the compositions or oral dosage forms of the present invention include, but are not limited to animal proteases, bacterial proteases, fungal proteases (e.g., an *Aspergillus melleus* protease), plant proteases, recombinant proteases (e.g., produced via recombinant DNA technology by a suitable host cell, selected from any one of bacteria, yeast, fungi, plant, insect or mammalian host cells in culture, or recombinant proteases which include an amino acid sequence that is homologous or substantially identical to a naturally occurring sequence, proteases encoded by a nucleic acid that is homologous or substantially identical to a naturally occurring protease-encoding nucleic acid, etc.), chemically modified proteases, or mixtures thereof.

The compositions or oral dosage forms of the present invention can comprise one or more lipases (i.e., one lipase, or two or more lipases), one or more amylases (i.e., one amylase, or two or more amylases), one or more proteases (i.e., one protease, or two or more proteases), mixtures of one or more lipases with one or more amylases, mixtures of one or more lipases with one or more proteases, mixtures of one or more amylases with one or more proteases, or mixtures of one or more lipases with one or more amylases and one or more proteases.

In one embodiment, the digestive enzyme is a porcine pancreatic extract comprising various lipases (e.g., lipase, colipase, phospholipase A2, cholesterol esterase), proteases (e.g., trypsin, chymotrypsin, carboxypeptidase A and B, elastase, kininogenase, trypsin inhibitor), amylases, and optionally nucleases (ribonuclease, deoxyribonuclease). In another embodiment, the digestive enzyme is substantially similar to human pancreatic fluid. In yet another embodiment, the digestive enzyme is pancrelipase USP. In still another embodiment, the digestive enzyme is pancrelipase USP having a lipase activity of 69-120 U USP/mg, amylase activity of greater than or equal to 216 U USP/mg, protease activity of greater than or equal to 264 U USP/mg, and total protease activity of greater than or equal to 264 U USP/mg.

In one embodiment, compositions of the present invention have total lipase, protease, and amylase activities as described in Table 1, below (where "total" activity refers to the combined activities of enteric leg coated and uncoated enzyme-containing beads):

TABLE 1

| | Formulation | | | | | | | |
|---|---|---|---|---|---|---|---|---|
| | 1 | | 2 | | 3 | | 4 | |
| | min | max | min | max | min | max | min | max |
| Activity (IU) | | | | | | | | |
| Lipase | 4500 | 5500 | 9000 | 11000 | 13500 | 16500 | 18000 | 22000 |
| Amylase | 8100 | 45000 | 17100 | 90000 | 26100 | 135000 | 35100 | 180000 |
| Protease | 8100 | 34000 | 17100 | 67000 | 26100 | 100000 | 35100 | 134000 |
| Ratio | | | | | | | | |
| Amylase/Lipase | 1.8 | 8.2 | 1.9 | 8.2 | 1.9 | 8.2 | 2.0 | 8.2 |
| Protease/Lipase | 1.8 | 6.2 | 1.9 | 6.1 | 1.9 | 6.1 | 2.0 | 6.1 |

In a particular embodiment, the compositions of the present invention comprise in total about 25,000 USP units of lipase and about 85,000 USP units of protease. In another embodiment the compositions of the present invention comprise in total about 20,000 USP units of lipase and 68,000 USP units of protease. In another embodiment the compositions of the present invention comprise in total about 15,000 USP units of lipase and 51,000 USP units of protease. In another embodiment the compositions of the present invention comprise in total about 10,000 USP units of lipase and 34,000 USP units of protease. In another embodiment the compositions of the present invention comprise in total about 5,000 USP units of lipase and 17,000 USP units of protease. The ratio of lipase or protease contained in enterically coated beads to lipase or protease contained in uncoated beads ranges from about 5/95 to about 50/50 (including about 5/90, about 10/90, about 15/85, about 20/80, about 25/75, about 30/70, about 35/65, about 40/60, about 45/55, or about 50/50), based on enzyme activity). For example, the approximate activities for lipase and protease in compositions according to the present invention are shown below in Table 2:

TABLE 2

| Formulation # | | Approx. Enterically Coated Bead Activity (USP units) | Approx. Uncoated Bead Activity (USP units) | Ratio Coated/Uncoated Beads |
|---|---|---|---|---|
| 1 | Lipase | 1000 | 19000 | 5/95 |
| | Protease | 3400 | 64600 | |
| 2 | Lipase | 2000 | 18000 | 10/90 |
| | Protease | 6800 | 61200 | |
| 3 | Lipase | 3000 | 17000 | 15/85 |
| | Protease | 10200 | 57800 | |
| 4 | Lipase | 4000 | 16000 | 20/80 |
| | Protease | 13600 | 54400 | |
| 5 | Lipase | 5000 | 15000 | 25/75 |
| | Protease | 17000 | 51000 | |
| 6 | Lipase | 6000 | 14000 | 30/70 |
| | Protease | 20400 | 47600 | |
| 7 | Lipase | 7000 | 13000 | 35/65 |
| | Protease | 23800 | 44200 | |
| 8 | Lipase | 8000 | 12000 | 40/60 |
| | Protease | 27200 | 40800 | |
| 9 | Lipase | 9000 | 11000 | 45/55 |
| | Protease | 30600 | 37400 | |
| 10 | Lipase | 10000 | 10000 | 50/50 |
| | Protease | 34000 | 34000 | |

Compositions of the present invention comprising suitable ratios of lipase and/or protease from enterically coated and uncoated beads can be provided by an individual dosage form, e.g. a capsule, comprising a mixture of enterically coated and uncoated digestive enzyme-containing beads, or can be provided by separate dosage forms, respectively comprising enterically coated digestive enzyme-containing beads, and uncoated digestive enzyme-containing beads. Alternatively, individual dosage forms containing different ratios of enterically coated and uncoated digestive enzyme-containing beads can be combined to provide a desired ratio of enterically coated and uncoated digestive enzyme-containing beads.

In other embodiments, the ratios of lipase:protease:amylase in the compositions or oral dosage forms of the present invention can be in the range of about 1:10:10 to about 10:1:1, or about 1.0:1.0:0.15 (based on enzyme activities). The ratio of amylase/lipase in the compositions or oral dosage forms of the present invention can range from about 1.8-8.2, for example about 1.9-8.2, and about 2.0-8.2. The ratio of protease/lipase in the compositions or oral dosage forms of the present invention can range from about 1.8-6.2, for example about 1.9-6.1, and about 2.0-6.1.

The total amount of digestive enzymes (by weight) in the compositions or oral dosage forms of the present invention can be about 20-100%, 20-90%, 20-80%, 20-70%, 20-60%, 20-50%, 20-40%, 20-30%, or about 20%, about 30%, about 40%, about 50%, about 60%, about 70%, about 80%, about 90%, or about 100%. In one embodiment, the total amount of digestive enzymes is 60-90%. In another embodiment, the total amount of digestive enzymes (e.g., pancrelipase) is about 68-72%.

In one embodiment, the compositions or oral dosage forms of the present invention, comprising at least one digestive enzyme, have a moisture content of about 3% or less, about 2.5% or less, about 2% or less, about 1.5% or less, or about 1% or less, inclusive of all ranges and subranges therebetween (i.e., any of about 2.5% to 3%, 2% to 3%, 1.5% to 3%, 1% to 3%, 2% to 2.5%, 1.5% to 2.5%, 1% to 2.5%, 1.5% to 2%, 1% to 2%, 1% to 1.5%, etc.). Compositions or oral dosage forms of the present invention, maintained at low moisture content, have been found to be substantially more stable compared to conventional compositions maintained at higher moisture contents, e.g. above about 3% or higher.

The term "moisture content", also referred to as "water content", means the amount of water that a composition contains. For compositions which do not change volume with changing moisture content, the moisture content can be expressed volumetrically (i.e., by volume) as the ratio of the mass of moisture to the dry volume of the material. For compositions that change volume with changing moisture content, the moisture content can be expressed gravimetrically (i.e., by weight) as the mass of water removed upon drying per unit dry mass of the specimen. Determination of moisture content can be achieved by any of the conventional methods known in the art. For example, the moisture content can be determined by chemical titration, such as Karl Fischer titration, in which a sample is dissolved in an electrochemical titration cell. Water from the sample is consumed in an electrochemical reaction whose endpoint is measured potentiometrically, thereby providing a direct measure of the amount of water in the sample. Alternatively, relatively simple thermogravimetric methods may be used such as "Loss on Drying" (LoD), in which the mass of a sample is measured prior to, and after controlled drying. The loss of mass after drying is attributed to loss of moisture. Commercially available moisture analyzers (e.g., available from Mettler Toledo, Sartorius AG, etc.) can also be used to determine moisture content. The moisture content of the compositions or oral dosage forms of the present invention can be measured by any suitable method known in the art, for example LoD.

In another embodiment, the compositions or oral dosage forms of the present invention, comprising at least one digestive enzyme, have a water activity of about 0.6 or less, about 0.5 or less, about 0.4 or less, about 0.3 or less, about 0.2 or less, or about 0.1 or less, inclusive of all ranges and subranges therebetween (i.e., any of about 0.5 to 0.6, 0.4 to 0.6, 0.3 to 0.6, 0.2 to 0.6, 0.1 to 0.6, 0.4 to 0.5, 0.3 to 0.5, 0.2 to 0.5, 0.1 to 0.5, 0.3 to 0.4, 0.2 to 0.4, 0.1 to 0.4, 0.2 to 0.3, 0.1 to 0.3, 0.1 to 0.2, etc.). Compositions or oral dosage forms of the present invention, maintained at a low water activity, have been found to be substantially more stable compared to conventional digestive enzyme compositions maintained at higher water activity levels.

Water activity, also referred to as "aw", is the relative availability of water in a substance. As used herein, the term "water activity" is defined as the vapor pressure of water in a sample divided by the vapor pressure of pure water at the same temperature. Pure distilled water has a water activity of exactly one. Water activity is temperature dependent. That is, water activity changes as the temperature changes. In the present invention, water activity is measured at a temperature ranging from about 0° C. to about 50° C., preferably from about 10° C. to about 40° C.

The water activity of a product can be determined by measuring the relative humidity of the air surrounding the sample at equilibrium. Accordingly, measurement of water activity in a sample is typically carried out in an enclosed (usually insulated) space where this equilibrium can take place. At equilibrium, the water activity of the sample and the relative humidity of the air are equal, and therefore a measurement of the equilibrium relative humidity (ERH) of the air in the chamber provides a measure of the water activity of the sample. At least two different types of water activity instruments are commercially available. One type of water activity instruments uses chilled-mirror dew point technology (e.g., AquaLab™ water activity meters available from Decagon Devices, Inc.) while others measure relative humidity with sensors that change electrical resistance or capacitance (e.g., water activity meters available from Rotronic). The water activity of the compositions or oral dosage forms of the present invention can be measured by any suitable method known in the art.

In another embodiment, the compositions or oral dosage forms of the present invention, comprising at least one stabilized digestive enzyme, exhibit a loss of enzyme activity of no more than about 25%, no more than about 20%, no more than about 15%, no more than about 12%, no more than about 10%, no more than about 8%, or no more than about 5%, after six months of accelerated stability testing.

The term "accelerated stability testing" or "accelerated storage testing" refers to test methods used to simulate the effects of relatively long-term storage conditions on enzyme activity, which can be carried out in a relatively short time. Accelerated stability testing methods are known in the art to be a reliable alternative to real-time stability testing, and can accurately predict the shelf life of biological products. Such "accelerated stability testing" conditions are known in the art and are in accordance with the International Conference for Harmonization of Technical Requirements for Registration of Pharmaceuticals for Human Use: Stability Testing of New Drug Substances and Products Q1A, herein incorporated by reference in its entirety.

One method of accelerated stability testing comprises storing samples of digestive enzyme composition in a sealed Nialene (nylon, aluminum, polyethylene laminate; GOGLIO SpA, Milan) bag at 40° C./75% relative humidity for 6 months.

After storage (or periodically during storage) the enzyme activity of the samples can be tested using conventional methods for assaying digestive enzyme activity (e.g., United States Pharmacopoeia, Pancrelipase: Assay for lipase activity; herein incorporated by reference in its entirety).

The compositions or oral dosage forms of the present invention can also further comprise one or more stabilizers which enhance or improve the stability of the compositions or oral dosage forms of the present invention. Non-limiting examples of suitable stabilizers include proline, trehalose, dextran, maltose, sucrose, mannitol, polyols, silica gel, aminoguanidine, pyridoxamine, anhydrous metal salts, such as sodium hydrogen carbonate magnesium oxide, calcium oxide, aluminum oxide and mixtures thereof. The one or more stabilizers can have a moisture content of about 3% or less and/or a water activity of 0.6 or less.

Non-limiting examples of suitable forms of trehalose which can be used in the compositions or oral dosage forms of the present invention include trehalose dihydrate (TD), amorphous trehalose (AT), anhydrous trehalose (e.g. anhydrous amorphous trehalose (AAT), anhydrous crystalline trehalose (ACT)). Powdered anhydrous trehalose may contain any AAT and/or ACT. As used herein, the term "trehalose" refers to any physical form of trehalose, including anhydrous, partially hydrated, fully hydrated and mixtures and solutions thereof. The term "anhydrous trehalose" refers to any physical form of trehalose containing less than 2% water. The anhydrous forms of trehalose may contain from 0-2% water. Amorphous trehalose contains about 2-9% water and trehalose dihydrate contains about 9-10% water. Anhydrous trehalose can be prepared as described in PCT/GB97/00367, herein incorporated by reference in its entirety. In one embodiment, the compositions or oral dosage forms of the present invention comprise one or more stabilized digestive enzymes and anhydrous trehalose.

The amount of anhydrous trehalose (AAT or ACT) in the composition of the present invention can be in the range of about 5-50%, 5-40%, 5-30%, 5-20%, 5-15%, 5-10%, 7-15%, or about 5%, about 7%, about 10%, about 15%, or about 20%.

The anhydrous trehalose can be incorporated into the compositions or oral dosage forms of the present invention as a powder. The particle size of the anhydrous trehalose powder can be in the range of about 2-2000 μm.

Compositions or oral dosage forms of the present invention comprising one or more stabilized digestive enzymes and anhydrous trehalose confer improved enzyme stability. It is believed that the anhydrous trehalose stabilizes the compositions or oral dosage forms of the present invention by absorbing or sequestering moisture from ambient humidity, or residual moisture from manufacturing or within the formulation itself.

Depending on the intended use and requirement of the compositions, the weight ratio of the stabilized digestive enzyme to the stabilizer ranges from about 99:1 to 80:20. The stabilizer can be incorporated into the compositions or oral dosage forms of the present invention by wet or dry blending at least one stabilized digestive enzyme with at least one stabilizer. In one embodiment, one or more stabilized digestive enzyme is dry blended with one or more stabilizer. In another embodiment, one or more stabilized digestive enzyme is wet blended with one or more stabilizer.

In addition to the stabilized digestive enzyme and/or stabilizer(s), the compositions or oral dosage forms of the present invention can further comprise one or more pharmaceutically acceptable excipients. The term "excipients" includes other pharmaceutically acceptable ingredients added to the active component(s) of a composition (e.g., the stabilized digestive enzymes) in order to improve processing, stability, palatability, etc. Non-limiting examples of suitable excipients include pharmaceutically acceptable binders, stabilizers, disintegrants, lubricants, glidants, diluents, and mixtures thereof etc. It will be appreciated by those skilled in the art of pharmaceutical formulations that a particular excipient may carry out multiple functions in the composition. So, for example a binder may also function as a diluent, etc. The excipients can have a moisture content of about 3% or less and/or a water activity of about 0.6 or less.

Non-limiting examples of suitable binders include starches, sugars (e.g. lactose), sugar alcohols (e.g. xylitol, sorbitol, maltitol), cellulose (e.g. microcrystalline cellulose), modified celluloses (e.g., hydroxypropylcellulose, carboxymethylcellulose sodium), alginic acid, polyvinyl pyrrolidone (povidone), and mixtures thereof. Non-limiting examples of suitable disintegrants include dibasic calcium phosphate, dibasic calcium phosphate dihydrate, tribasic calcium phosphate, alginic acid, hydroxypropylcellulose, carboxymethylcellulose calcium, carboxymethylcellulose sodium, cross-linked carboxymethylcellulose sodium, swellable ion exchange resins, alginates, formaldehyde-casein, cellulose, croscarmellose sodium, crospovidone (e.g., cross-linked polyvinyl pyrrolidone), microcrystalline cellulose, sodium carboxymethyl starch, sodium starch glycolate, starches (corn starch, rice starch), and mixtures thereof. Non-limiting examples of suitable lubricants include calcium stearate, magnesium stearate, sodium stearyl fumarate, stearic acid, zinc stearate, talc, waxes, STEROTEX®, STEAROWET®, and mixtures thereof. Non-limiting examples of suitable glidants include colloidal silicon dioxide, talc, and mixtures thereof. Non-limiting examples of suitable diluents include mannitol, sucrose, anhydrous dibasic calcium phosphate, anhydrous dibasic calcium phosphate dihydrate, tribasic calcium phosphate, cellulose, lactose, magnesium carbonate, microcrystalline cellulose, and mixtures thereof. Non-limiting examples of suitable stabilizers include trehalose, proline, dextran, maltose, sucrose, mannitol, polyols, silica gel, aminoguanidine, pyridoxamine, and mixtures thereof.

In one embodiment, the disintegrant is crospovidone (e.g., POLYPLASDONE XL, POLYPLASDONE XL-10). In another embodiment, the disintegrant is croscarmellose sodium (e.g., AC-DI-SOL). In another embodiment, the disintegrant is sodium starch glycolate (e.g., EXPLOTAB, EXPLOTAB CV). In another embodiment, the compositions or oral dosage forms of the present invention can comprise a combination of disintegrants such as microcrystalline cellulose and sodium starch glycolate or croscarmellose sodium and crospovidone.

The amount of disintegrant can be in the range of about any of about 0.1-30%, 1%-30%, 1%-25%, 1%-20%, 1%-15%, 1%-10%, 1%-5%, 5%-10%, 5%-15%, 5%-20%, 5%-25%, or 5%-30%. In one embodiment, the amount of disintegrant is about 2%-4%, or about 2%-3%, or about 2.5%.

Non-limiting examples of suitable diluents include microcrystalline cellulose, starch, calcium phosphate, lactose, sucrose, mannitol, sorbitol, and combinations thereof. In one embodiment, the diluent is microcrystalline cellulose (e.g. Avicel). In another embodiment, the diluent is starch. In another embodiment, the diluent is lactose (e.g., Pharmatol). In another embodiment, the compositions or oral dosage forms of the present invention can comprise a combination of diluents such as microcrystalline cellulose, starch and lactose.

The amount of diluent can be in the range of about any of about 0.1-99%, 1%-30%, 1%-25%, 1%-20%, 1%-15%, 1%-10%, 1%-5%, 5%-10%, 5%-15%, 5%-20%, 5%-25%, or 5%-30%. In one embodiment, the amount of diluent is about 2%-5%, 3%-5%, or about 4%.

One or more of the excipients of the compositions or oral dosage forms of the present invention can function as a desiccant to further stabilized the composition. Suitable excipients useful as desiccants include any pharmaceutically acceptable excipient that binds water tightly, or reduces the water activity of a composition. For example, the composition of the present invention can include about 1-4% silica gel, or about 2.5% silica gel.

As described herein, the multi-particulate compositions of the present invention comprise a first population of enterically coated digestive enzyme-containing beads, and a second population of uncoated digestive enzyme-containing beads. The enterically coated digestive enzyme-containing beads comprise a core and an enteric coating disposed over the core. The core comprises digestive enzymes, e.g. lipase, protease, and amylase, and optionally additional excipients as described herein. The enteric coating comprises at least one enteric polymer, and optionally a plasticizer and inorganic material as described herein.

The uncoated digestive enzyme-containing beads can be the same as the core of the enterically coated digestive enzyme-containing beads prior to coating, or can have a different composition. In one embodiment, the uncoated digestive enzyme-containing beads and the core of the enterically coated digestive enzyme-containing beads are substantially the same. In some embodiments, the uncoated digestive enzyme-containing beads are optionally coated with a sealant layer, e.g. comprising hydroxypropyl methylcellulose.

The enterically coated and uncoated digestive enzyme-containing beads can be prepared as described herein, or as described in any of U.S. Patent Publication Nos. 2008/0299185, 2008/0274174, or 2008/0279953.

The compositions of the present invention can be prepared in any suitable oral dosage form. Non-limiting examples of suitable dosage forms include tablets, capsules or sachets. When the compositions of the present invention are formulated as tablets, the enterically coated and uncoated digestive enzyme-containing beads, and optional excipients, can be "tabletted" (i.e., formed into tablets) using methods known in the art. In a particular embodiment, the compositions of the present invention are filled into a capsule using methods known in the art.

As described herein, the multi-particulate composition of the present invention comprises enterically coated and uncoated digestive enzyme-containing beads. The term "beads" refers to any suitable particulate form comprising digestive enzymes, for example a powder, a granulate, microtablets (as described herein), or minitablets (as described herein). The term "granulate" refers to an aggregated particle comprised of primary particles, formed by conventional granulation processes known in the art, and may include an optional binder.

The enterically coated digestive enzyme-containing beads are coated with an enteric coating comprising at least one enteric polymer. The term "enteric polymer" means a polymer that protects the digestive enzymes from gastric contents, for example a polymer that is stable at acidic pH, but can break down rapidly at higher pH or a polymer whose rate of hydration or erosion is slow enough to ensure that contact of gastric contents with the digestive enzymes is relatively minor while it is in the stomach, as opposed to the remainder of the gastro-intestinal tract. Non-limiting examples of enteric polymers include those known in the art, such as modified or unmodified natural polymers such as cellulose acetate phthalate, hydroxypropylmethylcellulose phthalate, hydroxypropylmethylcellulose acetate succinate, and shellac; or synthetic polymers such as acrylic polymers or copolymers methacrylic acid polymers and copolymers, methyl-methacrylate copolymers, and methacrylic acid/methylmethacrylate copolymers (e.g., EUDRAGIT® L or S).

The enteric polymer coating can be a synthetic polymer, optionally including an inorganic material, such as an alkalinizing agent. The resulting coated particles provide enterically coated beads comprising a core which comprises the stabilized digestive enzyme(s) and an enteric coating encapsulating the core. The coated stabilized digestive enzyme particles can then be formulated into tablets or capsules.

The enteric polymer and the at least one inorganic material impart enteric properties to the enterically coated beads of the present invention. That is, the enteric coating will act as a barrier protecting the encapsulated digestive enzymes from the acidic environment of the stomach and substantially prevent the release of the digestive enzymes before they reaches the small intestine (i.e., the release of digestive enzyme in the stomach is less than about 10-20% of the total amount of digestive enzyme in the enterically coated bead portion of the composition).

The inorganic material can include, for example, silicon dioxide, sodium salts, calcium salts, magnesium salts, aluminum salts, aluminum hydroxides, calcium hydroxides magnesium hydroxides, talc, and combinations thereof. In one embodiment, the inorganic material is talc.

The ratio of the enteric polymer and the at least one inorganic material may be in a range of from about 10:1 to about 1:60 by weight. In another embodiment, the ratio of the enteric polymer and the at least one inorganic material ranges from about 8:1 to about 1:50 by weight. In another embodiment, the ratio of the enteric polymer and the at least one inorganic material ranges from about 6:1 to about 1:40 by weight. In another embodiment, the ratio of the enteric polymer and the at least one inorganic material ranges from about 5:1 to about 1:30 by weight. In another embodiment, the ratio of the enteric polymer and the at least one inorganic material ranges from about 4:1 to about 1:25 by weight. In another embodiment, the ratio of the enteric polymer and the at least one inorganic material ranges from about 4:1 to about 1:9 by weight. In another embodiment, the ratio of the enteric polymer and the at least one inorganic material ranges from about 10:4 to about 10:7 by weight.

In one embodiment, the compositions or oral dosage forms of the present invention comprise stabilized digestive enzyme particles coated with an enteric coating comprising an enteric polymer and an inorganic material such as talc. In a particular embodiment, the inorganic material of the enteric coating comprises about 1-10% by weight of the weight of the total weight of the particles. In another embodiment the inorganic material comprises about 3, about 5, about 7, or about 10% by weight of the particles. In still other embodiments, the inorganic material comprises about 20-60% of the dry coating weight. In still other embodiments, the alkalinizing agent is about 25%, about 30%, about 35%, about 40%, about 45%, about 50%, or about 55% of the dry coating weight (inclusive of all ranges, subranges, and values therebetween). In a particular embodiment, the inorganic material is talc. In still another particular embodiment, the dry coating of the particles comprises about 31% to about 35% talc.

In some embodiments, the coating is substantially free of plasticizer. In other embodiments of the present invention, the coating further comprises a plasticizer. Examples of suitable plasticizers include, but are not limited to triacetin, tributyl citrate, tri-ethyl citrate, acetyl tri-n-butyl citrate, diethyl phthalate, dibutyl sebacate, polyethylene glycol, polypropylene glycol, castor oil, acetylated mono-glyceride, acetylated di-glyceride, and mixtures thereof.

The dosage forms of the present invention can be capsules containing the composition of the present invention (e.g., particles of the stabilized digestive enzyme composition, a portion of which are coated with an enteric polymer and an inorganic material). The capsules themselves can be comprised of any conventional biodegradable material known in the art, for example, gelatin, polysaccharides such as pullulan, or modified cellulosic materials such as hydroxypropylmethylcellulose. In order to improve the stability of the stabilized digestive enzymes, the capsule can be dried prior to filling, or a capsule comprised of a low moisture content material can be selected. In one embodiment of the dosage form of the present invention, the capsule is comprised of hydroxypropylmethylcellulose. In another embodiment of the dosage form of the present invention, the capsule is comprised of hydroxypropylmethylcellulose having a water content of about 6% or less, for example about any of 4% or less, 2% or less, or 2-6%, or 4-6%. In another embodiment, the capsule is comprised of hydroxypropylmethylcellulose having a water content of less than about 2%.

The dosage forms of the present invention can comprise a single digestive enzyme, or mixtures of digestive enzymes. The uncoated beads and the core portion of the enterically coated beads of the multi-particulate composition of the present invention can each have nominally the same composition, or can have different compositions. For example the dosage form can be a capsule filled with enterically coated beads, each of which has a core comprising pancrelipase, and uncoated beads comprising pancrelipase. Alternatively, the dosage form can be a capsule filled with enterically coated beads and uncoated beads, wherein some of the enterically coated beads have a core comprising pancrelipase, whereas other enterically coated beads have cores comprising a different lipase, or proteases or amylases. Similarly, some of the uncoated beads can comprise pancrelipase, while other uncoated beads comprise a different lipase, protease, or amylases. Alternatively, the enterically coated beads can each have cores comprising pancrelipase, whereas some or all of the uncoated beads can comprise a different enzyme composition, for example a protease. Any suitable combination of coated and uncoated beads of different compositions can be used to provide the desired therapeutic effect.

In addition, the individual enterically coated beads can each have the same enteric coating composition, or can include mixtures of enterically coated beads, some of which have a different enteric coating composition. Any suitable combination of enteric coating compositions can be used to provide the desired type of therapeutic effect.

The core of the enterically coated or the uncoated beads can have any suitable particle size or shape. For example, the beads can be in the form of a coated powder having a particle size range of about 50-5000 microns, or can be in the form of "minitabs" which have a nominal particle diameter in the range of about 2-5 mm. For other applications, the core of the coated particles can be "microtabs" which have nominal particle diameters of less than about 2 mm, for example about 1-2 mm.

The digestive enzyme-containing beads (e.g. the uncoated digestive enzyme-containing beads or the cores of the enterically coated digestive enzyme-containing beads) can comprise a digestive enzyme, at least one disintegrant, at least one polymeric binder or diluent, and optionally at least one plasticizer, optionally at least one glidant, and optionally at least one lubricant. In one embodiment, the enterically coated or uncoated beads can comprise about 60-90% of digestive enzyme, about 1-4% of at least one disintegrant, about 2-6% of at least one polymeric binder or diluent, and optionally about 0.5-1.0% of at least one plasticizer, optionally about 0.2-0.6% of at least one glidant, and optionally about 0.2-0.6% of at least one lubricant. For example, the digestive enzyme-containing beads can comprise about 60-90% pancrelipase, about 1-4% of croscarmellose sodium, about 0.5-1.0% of hydrogenated castor oil, about 0.2-0.6% of colloidal silicon dioxide, about 2-6% of microcrystalline cellulose, and about 0.2-0.6% of magnesium stearate. The enteric coating can comprise at least one enteric polymer, about 20-35% of at least one inorganic material (based on the dry weight of the enteric coating), and optionally at least one plasticizer. In one embodiment, the enteric coating can comprise about 10-20% of a least one enteric polymer, about 4-10% of a least one alkalinizing agent, and about 1-2% of a least one plasticizer (based on the total weight of the coated beads). For example, the coating can comprise about 10-20% of hydroxypropylmethylcellulose phthalate, about 4-10% of talc, and about 1-2% of triethyl citrate (based on the total weight of the coated beads). The plurality of coated digestive enzyme-containing beads can then be combined with uncoated digestive enzyme-containing beads and formed into a tablet, or filled into a capsule. In one embodiment, the capsule comprises hydroxypropylmethylcellulose.

The compositions of the present invention, and dosage forms comprising the compositions of the present invention, have improved stability compared to conventional digestive enzyme (e.g., pancrelipase) compositions and dosage forms. Consequently, the dosage forms of the present invention do not require "overfilling" (i.e., zero-overfill), as do conventional digestive enzyme dosage forms, to deliver a clinically useful amount of digestive enzyme to a patient in need thereof. Conventional digestive enzyme compositions and dosage forms require overfilling levels of as much as 65% (i.e., 165% of the required dose of digestive enzyme) to compensate for the poor enzyme stability. As a result, there is uncertainty as to the dose delivered by conventional digestive enzyme compositions. Thus, conventional "overfilled" dosage forms can deliver higher than the intended dose of digestive enzymes shortly after manufacture, but over time, the enzyme activity can fall below the intended dose.

In one embodiment, the dosage forms comprising the compositions of the present invention are substantially zero-overfill. The term "substantially zero-overfill" means compositions of the present invention in which the amount of additional digestive enzyme activity (i.e., the amount of additional enzyme activity above the intended dose) is less than or equal to about 10%, i.e., about 10%, less than about 10%, less than or equal to about 9%, less than or equal to about 8%, less than or equal to about 7%, less than or equal to about 6%, less than or equal to about 5%, less than or equal to about 4%, less than or equal to about 3%, less than or equal to about 2%, less than or equal to about 1%, or about 0%. So, for example, if the intended dose is about 4500 IU lipase, the substantially zero-overfill dosage forms of the present invention may contain less than or equal to about 4950 IU lipase (i.e., less than or equal to 110% of 4500 IU lipase). In another embodiment, the zero-overfill dosage form contains 4500 IU lipase.

The compositions or dosage forms of the present invention comprising a combination of enterically coated and uncoated digestive enzyme-containing beads also has the advantage of effectively treating both pancreatic pain, as well as the underlying nutritional deficiency (e.g., fat malabsorption) at substantially lower doses than are conventionally considered effective. For example, previous studies investigating the treatment of pancreatic pain with uncoated pancreatic enzyme compositions required dosage at 64,000 units of lipase and 240,000 units of protease per meal. The treatment of fat malabsorption typically requires doses of about 35,000-175,000 units of lipase per meal. Accordingly, treatment of both pancreatic pain and fat malabsorption would require about 99,000-239,000 lipase units per meal (combined uncoated and coated pancreatic enzyme). Surprisingly, the present inventors have found that total lipase doses of about 80,000 lipase units are effective in treating pancreatic pain and fat malabsorption when about 2000-20,000 lipase units are provided in the form of enterically coated beads and about 76,000-60,000 lipase units are provided in the form of uncoated beads (i.e., 5/95 to about 25/75 enterically coated lipase/uncoated lipase). These doses may be given with each meal, or dosed at multiple times during a single day The compositions or dosage forms (e.g., tablets or capsules) of the present invention can be stored in any suitable package. For example, the package can be a glass or plastic jar with a threaded or press-fit closure. Alternatively, the compositions or dosage forms of the present invention can be packaged as a unit dosage form in "blister packs". Applicants have found that improved stability of the digestive enzyme compositions or dosage forms can be provided by providing a moisture-proof seal, and/or a moisture-proof package. Non-limiting examples of suitable moisture-proof packages include glass jars, plastic jars incorporating moisture barrier resins or coatings, aluminized plastic (e.g., Mylar) packaging, etc. The term "moisture-proof" refers to a package which has a permeability to water of less than about 0.5 mg water per $cm^3$ of container volume per year.

Containers (e.g., bottles) can be closed with any suitable closure, especially closures which minimize the ingress of moisture during storage. For example, the compositions or dosage forms of the present invention can be closed with a closure such as Saf-Cap III-A (Van Blarcom Closures, Inc.), containing HS 035 Heat Seal/20F (SANCAP Liner Technology, Inc.) printed as a sealing liner.

In order to ensure package integrity and minimize moisture ingress during storage, sealed packages containing the compositions or dosage forms of the present invention can be leak-tested after dispensing the composition or dosage form of the present invention and sealing the package. For example, the sealed packages can be tested by applying a controlled vacuum to the closure, and detecting the decrease in vacuum over time. Suitable leak-testing equipment includes those manufactured by Bonfiglioli (e.g., model LF-01-PKV or model PKV 516).

Packages containing the compositions or dosage forms of the present invention can also contain a desiccant (i.e., a substance which absorbs, reacts with, or adsorbs water) capable of reducing the humidity inside the package, for example a desiccant capsule, capable of "scavenging" moisture from the atmosphere sealed inside the package. Non-limiting examples of suitable desiccants which can be placed inside such packages include zeolites (e.g., molecular sieves such as 4 Å molecular sieves), clay (e.g., montmorillonite clay), silica gel, activated carbon, or combinations thereof. In one embodiment, the desiccant comprises molecular sieves.

In addition, it is common practice when packaging oral pharmaceutical unit doses to add a "plug" of a cellulosic material, such as cotton, into the top of the container to fill the empty space at the top of the container, thereby minimizing movement of the contents. Cellulosic materials are somewhat hygroscopic, and can act as a "reservoir" of moisture inside the package. Accordingly, in one embodiment of the packages of the present invention, no cellulosic or cotton "plug" is present in the package. In another embodiment of the packages of the present invention, the packages lack a cellulosic or cotton plug, and contain a desiccant.

The compositions of the present invention can be prepared using conventional techniques, but modified as indicated herein to provide moisture contents of about 3% or less, water activities of about 0.6 or less, or provide stabilized digestive enzyme compositions which exhibit a loss of activity of no more than about 15% after three months accelerated stability testing. For example, beads of digestive enzymes (e.g., pancrelipase) can be coated in a fluidized bed coating apparatus equipped with a dehumidifier. In one embodiment, the coating apparatus is operated in an atmosphere having a water content of about 4 $g/m^3$ or less, about 3.5 $g/m^3$ or less, about 3 $g/m^3$ or less, about 2.5 $g/m^3$ or less, about 2.0 $g/m^3$ or less, about 1.5 $g/m^3$ or less, about 1.0 $g/m^3$ or less, or about 0.5 $g/m^3$ or less, including all ranges and subranges therebetween. The atmosphere in which the coating is carried out can comprise dehumidified air, dehumidified nitrogen, or another dehumidified inert gas.

The coating can be applied as a solution of the enteric polymer (and optionally a suspended inorganic material) in an organic solvent such as an alcohol (e.g. ethanol), a ketone (e.g. acetone), methylene chloride, or mixtures thereof (e.g. mixtures of acetone ethanol).

The compositions of the present invention are effective for treating pancreatic pain (i.e., reducing or relieving pancreatin pain, and also provide improved absorption of fats, proteins, and carbohydrates in patients suffering from conditions or disorders associated with a digestive enzyme deficiency. In one embodiment, compositions of the invention, in particular pancrelipase or pancreatin compositions, may be used to treat pancreatic pain, for example pancreatic pain associated with exocrine pancreatic insufficiency (EPI) associated with various diseases or conditions. Such diseases include, but are not limited to cystic fibrosis (CF) or pancreatic insufficiency related to alcohol abuse.

In some embodiments, such compositions may substantially alleviate pancreatic pain alone, or pancreatic pain in combination with malabsorption (e.g. of fats) associated with EPI in cystic fibrosis patients and other patients, including pediatric patients. In some embodiments, such compositions may increase the coefficient of fat absorption (CFA) to at least about 85% or more in cystic fibrosis patients. Such results may be achieved when co-administered with other agents or compositions, or may be achieved without co-administration with other agents. In one embodiment, such CFA results are achieved without co-administration of proton pump inhibitors such as Prilosec®, Nexium®, and the like.

For patients identified as having low GI pH levels (e.g., GI pH levels<about 4), improved results may be obtained by administering the compositions or dosage forms of the present invention together with proton pump inhibitors, antacids, and other drugs which increase the pH of the GI tract. For example, the compositions or dosage forms of the present invention can be administered separately from the proton pump inhibitors, antacid, or other drugs (either prior to, concurrently with, or after administration of the proton pump inhibitor, antacid, etc.). Alternatively, the proton pump inhibitor, antacid, or other drug can be combined with the pancreatin composition of the present invention as a single dosage form.

In yet another embodiment, the present invention provides a method of treating or preventing pancreatic pain, and optionally a disorder associated with a digestive enzyme deficiency comprising administering a composition of the present invention to a mammal in need thereof. In one embodiment, the mammal is a human.

In another embodiment, the present invention provides a method of treating or preventing pancreatic pain and/or treating a disorder associated with digestive enzyme deficiency, comprising administering low doses of pancreatic enzyme (e.g. 7×5000 USP lipase unit capsules as described herein, or similar doses of commercial compositions known in the art such as CREON® 1206, 1212, or 1224; ULTRASE®, VIOKASE®, etc.) to a patient in need thereof.

In yet another embodiment, the present invention provides a method of treating or preventing pancreatic pain, and optionally a disorder associated with a digestive enzyme deficiency comprising administering a composition or dosage form of the present invention to a mammal in need thereof, wherein the composition or dosage form of the present invention comprises, in addition to at least one digestive enzyme, a proton pump inhibitor, antacid, or other medicament which increases GI pH. In still another embodiment, the present invention provides a method of treating or preventing a disorder associated with a digestive enzyme deficiency, comprising administering a composition or dosage form of the present invention, in combination with a dosage form comprising a proton pump inhibitor, antacid, or other medicament which increases GI pH.

Disorders which cause or are associated with pancreatic pain, and which can be treated with the composition or dosage form of the present invention include conditions in which the patient has no or low levels of digestive enzymes or in which patients require digestive enzyme supplementation. For example, such conditions can include cystic fibrosis, chronic pancreatitis, other pancreatic diseases (e.g., hereditary, post-traumatic and allograft pancreatitis, hemochromatosis, Shwachman syndrome, lipomatosis, or hyperparathyroidism), side-effects of cancer or cancer treatment, side-effects of surgery (e.g., gastrointestinal bypass surgery, Whipple procedure, total pancreatectomy, etc.) or other conditions in which pancreatic enzymes cannot reach the intestine, poor mixing (e.g., Billroth II gastrectomy, other types of gastric by pass surgery, gastrinoma, etc.) side effects of drug treatments such as treatment with metformin or those drugs used to treat the symptoms of HIV and autoimmune diseases such as diabetes in which the pancreas may be compromised, obstruction (e.g., pancreatic and biliary duct lithiasis, pancreatic and duodenal neoplasms, ductal stenosis), malabsorption associated with celiac disease, food allergies and aging.

The amount of the composition or dosage form of the present invention administered daily to mammals (e.g., humans) depends upon the intended result. The skilled physician will be capable of prescribing the required dose based on his diagnosis of the condition to be treated.

For example, for the treatment of digestive enzyme insufficiency in humans (e.g., related to cystic fibrosis) the typical starting dose should be 500 to 1000 lipase units/kg/meal, with the total dose not exceeding 2500 lipase units/kg/meal or 4000 lipase units/g fat/meal in accordance with the recommendations of the US FDA. Typically, a patient should receive at least 4 dosage forms per day, preferably administered with food.

In particular embodiments, the dose will be about 80,000 lipase units and about 272,000 protease units per meal, wherein about 5-25% of the enzyme (based on activity) is provided in the form of enterically coated beads, and about 95-75% of the enzyme is provided in the form of the coated beads.

In other embodiments, the present invention is directed to a method of treating pancreatic exocrine insufficiency, for example caused by any of the conditions described herein, with low doses of enterically coated digestive enzyme composition, for example the enterically coated beads described herein. Conventional doses for treating pancreatic insufficiency, as described herein, range from about 500 to 1000 lipase units/kg/meal. For example, the FDA label for CREON® pancrelipase capsules states that enzyme dosing for adults "should begin with 500 lipase units/kg of body weight per meal for those older than age 4 years to a maximum of 2,500 lipase units/kg of body weight per meal". Thus, for a 70 kg adult, eating 3½ meals/day (i.e., 3 meals and 1 snack), the recommended daily dosage of CREON® pancrelipase would range from about 122,500 lipase units to about 612,500 lipase units. As described herein, the present inventors have surprisingly found that substantially lower doses of enterically coated digestive enzyme preparations are effective in treating pancreatic exocrine insufficiency. Accordingly, doses of enterically coated digestive enzyme as low as about 100 lipase units/kg/meal, and up to about 300 lipase units/kg/meal are effective in treating pancreatic exocrine insufficiency, but substantially reducing the "pill burden" on patients suffering from such conditions. Suitable doses include about 100, about 110, about 120, about 130, about 140, about 150, about 160, about 170, about 180, about 190, about 200, about to 10, up to 20, about 230, about 240, about 250, about 260, about 270, about 280, about 290, or about 300 lipase units/kg/meal, inclusive of all ranges and subranges therebetween, can be administered to a patient in need thereof.

EXAMPLES

Example 1

Uncoated and Enterically Coated Pancrelipase Minitablets

Pancrelipase MT (minitablets) is a blend of pancrelipase raw material (e.g., obtained from Nordmark) and excipients (e.g., croscarmellose sodium, hydrogenated castor oil, colloidal silicon dioxide, microcrystalline cellulose, and magnesium stearate) tabletted using round 2 mm diameter beveled punches. The physical characteristics of the Pancrelipase MT before coating are shown below in Table 3.

TABLE 3

| | |
|---|---|
| Diameter | 2.0 mm |
| Weight (of 10 MT) | 0.074-0.086 g |
| Thickness (mean value of 10 MT) | 2.2 ± 0.2 mm |
| Hardness | 0.5-2.0 Kp |
| Friability* (20 g of MT-30 min at 25 rpm) | 0.0-2.5% |

*USP method

Pancrelipase MT was coated with a coating formulation (Table 4) using a fluidized bed Glatt-GPCG1 apparatus equipped with a Munters ML 1350 dehumidifier in the process airflow. The coating process was carried out with process air at three different moisture contents (Table 5). For each batch, the coating weight was approximately 15% of the total weight of the coated beads. The composition of the coated beads for each set a process conditions is approximately the same (Table 6), and appeared uniform, smooth and homogeneous after microscopic examination.

TABLE 4

| Material | % (w/w) |
|---|---|
| Hypromellose Phthalate (HP55) | 10.19 |
| Triethyl citrate (TEC) | 1.02 |
| Talc | 1.02 |
| Ethanol 96% | 79.78 |
| Acetone | 7.99 |
| | 100.00 |

TABLE 5

| Lot | Process Air Moisture Content (g/m$^3$) |
|---|---|
| P9A165 | 8.8 |
| P9A167 | 0.4 |
| P9A170 | 3.6 |

TABLE 6

| Material | Coating Composition % (w/w) |
|---|---|
| Pancrelipase MT | 85.00 |
| Hypromellose Phthalate (HP55) | 12.50 |
| Triethyl citrate (TEC) | 1.25 |
| Talc | 1.25 |
| | 100.00 |

The three sets of samples (i.e., P9A165, P9A167, and P9A170) showed residual moisture contents corresponding to the moisture content of the processing air flow (Table 7).

TABLE 7

| Lot | Loss on Drying (%) |
|---|---|
| P9A165 | 2.8 |
| P9A167 | 1.1 |
| P9A170 | 1.7 |

Example 2

Enterically Coated Minitablets

Pancrelipase MT particles were coated with two coating compositions containing different amounts of talc (Table 8).

TABLE 8

| | Composition % (w/w) | |
| --- | --- | --- |
| Material | Low talc content | High talc content |
| Hypromellose Phthalate (HP55) | 10.190 | 5.825 |
| Triethyl citrate (TEC) | 1.020 | 0.580 |
| Talc | 1.020 | 5.825 |
| Ethanol 96% | 79.780 | 79.780 |
| Acetone | 7.990 | 7.990 |
| | 100.000 | 100.000 |
| HP:TEC:Talc ratio | 10:1:1 | 10:1:10 |
| Total solid content | 12.23% | 12.23% |

Coating trials were carried out using a fluidized bed Glatt-GPCG1 apparatus equipped with a Munters ML 1350 dehumidifier in order to assure process air flow at a low moisture content (i.e., lower than 1 g/m$^3$). Coating weights were approximately 15%. The theoretical composition of the two batches is reported in Table 9. Microscopic examination indicated that the coatings on all samples were smooth and homogeneous. Residual moisture contents were measured by loss on drying (Table 10).

TABLE 9

| | Batch | |
| --- | --- | --- |
| | P9A230 | P9A240 |
| | Low talc content | High talc content |
| Material | Composition % (w/w) | |
| Pancrelipase MT | 85.000 | 85.000 |
| Hypromellose Phthalate (HP55) | 12.500 | 7.143 |
| Triethyl citrate (TEC) | 1.250 | 0.714 |
| Talc | 1.250 | 7.143 |
| | 100.000 | 100.000 |

TABLE 10

| Lot | Loss on Drying (%) |
| --- | --- |
| P9A230 | 0.9 |
| P9A240 | 0.9 |

Example 3

Enterically Coated Minitablets

"High talc" and "low talc" coating compositions similar to those described in table 6, except that the ethanol (96% ethanol, 4% water)/acetone solvent was replaced with 100% acetone (Table 11).

TABLE 11

| | Composition % (w/w) | |
| --- | --- | --- |
| Material | Low talc content | High talc content |
| Hypromellose Phthalate (HP55) | 10.190 | 5.825 |
| Triethyl citrate (TEC) | 1.020 | 0.580 |
| Talc | 1.020 | 5.825 |
| Acetone | 87.770 | 87.770 |
| | 100.000 | 100.000 |
| HP:TEC:Talc ratio | 10:1:1 | 10:1:10 |
| Total solid content | 12.23% | 12.23% |

The coating trials were carried out using a fluidized bed Glatt-GPCG1 apparatus equipped with a Munters ML 1350 dehumidifier in order to assure process air flow at a low moisture content (lower than 1 g/m$^3$). Coating weights were approximately 15%. The theoretical composition of the two batches is reported in Table 12.

TABLE 12

| | Batch | |
| --- | --- | --- |
| | P9A318 | P9A352 |
| | Low talc content | High talc content |
| Material | Composition % (w/w) | |
| Pancrelipase MT | 85.000 | 85.000 |
| Hypromellose Phthalate (HP55) | 12.500 | 7.143 |
| Triethyl citrate (TEC) | 1.250 | 0.714 |
| Talc | 1.250 | 7.143 |
| | 100.000 | 100.000 |

Example 7

Enterically Coated Minitablets

Pancrelipase MT particles were coated with two coating compositions having a level of talc intermediate between the "low" and "high" levels employed above (HP55:TEC:Talc=10:1:5), using either acetone or a mixture of ethanol/acetone as the coating solvent. The theoretical composition of the two coating suspensions shown in Table 13, below.

TABLE 13

| | Composition % (w/w) Intermediate talc content | |
| --- | --- | --- |
| Material | | |
| Hypromellose Phthalate (HP55) | 7.644 | 7.644 |
| Triethyl citrate (TEC) | 0.764 | 0.764 |
| Talc | 3.822 | 3.822 |
| Ethanol | 79.780 | |
| Acetone | 7.990 | 87.770 |
| | 100.000 | 100.000 |
| HP:TEC:Talc ratio | 10:1:5 | 10:1:5 |
| Total solid content | 12.23% | 12.23% |

The coating trials were carried out using a fluidized bed Glatt-GPCG1 apparatus equipped with a Munters ML 1350 dehumidifier in order to assure process air flow at a low moisture content (lower than 1 g/m$^3$).

The batches were prepared by coating the Pancrelipase MT at a coating weight of approximately 15%. Three batches were prepared with an ethanol/acetone coating solvent and three batches were prepared with an acetone coating solvent.

The theoretical composition, which was the same for all six batches, is shown below in Table 14.

TABLE 14

| Material | Batch | |
|---|---|---|
| | P9A483-P9A485-P9A486 Ethanol/Acetone as solvent | P9A405-P9A476-P9A477 Acetone as solvent |
| | Composition % (w/w) | |
| Pancrelipase MT | 85.00 | 85.00 |
| Hypromellose Phthalate (HP55) | 9.37 | 9.37 |
| Triethyl citrate (TEC) | 0.94 | 0.94 |
| Talc | 4.69 | 4.69 |
| | 100.00 | 100.00 |

Microscopic examination of the coating for all six samples appeared smooth and homogeneous.

Example 8

Enterically Coated and Uncoated Microtablets

Microtablets

To provide further choices for dosage formulations were made in which the dimensions of the tablets was significantly reduced. The pancrelipase blend was tabletted with round 1.5 mm diameter, 1.2 mm radius of curvature punches.

The compression parameters were set to obtain microtablets ("µT") with friability lower than 2.5% (USP method). The characteristics of Lot 9A402 are shown in Table 15.

TABLE 15

| Lot P9A402 | Values |
|---|---|
| Diameter | 1.5 mm |
| Weight (of 20 µT) | 0.071 g (0.070-0.073) |
| Thickness (as mean value of 20 µT) | 1.73 mm (1.70-1.77) |
| Hardness (as mean value of 20 µT) | 4 Newton (3-5) |
| Friability (20 g of µT-30 min at 25 rpm) | 1.80% |

Lot P9A402 was coated in a fluid bed Glatt-GPCG1 apparatus equipped with a Munters ML 1350 dehumidifier in order to assure process air flow at low moisture content (lower than 1 g/m$^3$) with a suspension having the composition shown in Table 4. A coating weight of 22% was obtained. Microscopic examination of the film coatings indicated that all of the samples appeared smooth and homogeneous.

The theoretical composition of the batch Lot P9A422 is shown in Table 16.

TABLE 16

| Lot P9A422 | Standard coat Composition % (w/w) |
|---|---|
| Pancrelipase MT | 78.00 |
| Hypromellose Phthalate (HP55) | 18.34 |
| Triethyl citrate (TEC) | 1.83 |
| Talc | 1.83 |
| | 100.000 |

Two other batches of enterically coated microtablets were prepared as described above, and their properties are shown below in Table 17.

TABLE 17

| Characteristics | Lot P9A457 | Lot P9A459 |
|---|---|---|
| Diameter | 1.5 mm | 1.5 mm |
| Weight (of 20 µT) | 0.072 g (0.070-0.073) | 0.071 g (0.070-0.074) |
| Thickness (as mean value of 20 µT) | 1.73 mm (1.67-1.83) | 1.74 mm (1.69-1.82) |
| Hardness (as mean value of 20 µT) | 5 Newton (3-6) | 5 Newton (4-6) |
| Friability (20 g of µT-30 min at 25 rpm) | 1.99% | 2.02% |

The microtablets prepared above were slightly oblong (see Table 15); the ratio between the microtablet thickness and diameter was between 1.22:1 and 1.15:1.

To further reduce the dimensions of the microtablets, new samples were prepared with ratios of thickness to diameter ratio nearer to 1:1 (Lot Q9A006), are shown below in Table 18.

TABLE 18

| Characteristics | Lot Q9A006 |
|---|---|
| Diameter | 1.5 mm |
| Weight (of 20 µT) | 0.060 g (0.058-0.062) |
| Thickness (as mean value of 20 µT) | 1.50 mm (1.45-1.58) |
| Hardness (as mean value of 20 µT) | 5 Newton (4-6) |
| Friability (20 g of µT-30 min at 25 rpm) | 1.63% |

Lot Q9A006 was coated with the compositions shown in Table 19 at a coating weight of 22%. The coating trials were carried out using a fluidized bed Glatt-GPCG1 apparatus equipped with a Munters ML 1350 dehumidifier in order to assure processing air flow at low moisture content (lower than 1 g/m$^3$).

The theoretical composition of the coated microtablet Lot Q9A019 was the same as that shown in Table 19. Microscopic examination indicated that the coatings were smooth and homogeneous.

TABLE 19

| Material | Composition % (w/w) Intermediate talc content |
|---|---|
| Hypromellose Phthalate (HP55) | 7.644 |
| Triethyl citrate (TEC) | 0.764 |
| Talc | 3.822 |
| Acetone | 87.770 |
| | 100.000 |
| HP:TEC:Talc ratio | 10:1:5 |
| Total solid content | 12.23% |

Example 9

Treatment with Combination of Enterically Coated and Uncoated Pancreatin

A Single-center, randomized, open-label, crossover, active-control study to evaluate the safety and efficacy of Composition A and Composition B, different pancreatic enzyme products (PEPs), is carried out in patients with chronic pancreatitis.

Each capsule of Composition A contains approximately 10 enteric coated small beads with a total of 10,000 USP Lipase Units and 34,000 USP Protease Units, and 10 non-coated beads 10,000 USP Lipase Units and 34,000 USP Protease Units. Each capsule of Composition B contains approximately 2 enteric coated small beads with a total of 2,000 USP Lipase Units and 6,800 USP Protease Units, and 18 non-coated beads with a total of 18,000 USP Lipase Units and 61,200 USP Protease Units. The individual current Pancreatic Enzyme Replacement Therapy (PERT) with enteric-coated PEP is used as the active control.

Group 1 is randomized to receive 4 capsules per meal Composition A, 16 capsules per day divided over 4 meals, and Group 2 is randomized to receive Composition B, 16 capsules per day divided over 4 meals. Group 3 is administered the same PERT at a fixed dose of capsules per day given prior to screening.

Efficacy is evaluated by quantifying pain severity as the number of pain episodes/day and severity of pain as measured on an 11-point Visual Analog Scale. The secondary objective is to measure malabsorption of fat by assessing CFA.

Patient inclusion criteria are as follows:

Diagnosis of CP confirmed by an abnormal ERP (modified Cambridge II or III) with concomitant steatorrhea with CFA ≤70% at baseline (>7 g fat in stool/day in patients with 100 g fat intake);

Recurrent chronic upper GI pain, frequency of at least 1 episode per day;

Are able to be switched from an existing marketed PEP treatment;

Are clinically stable with no evidence of concomitant illness or acute upper or lower respiratory tract infection during the 7 day interval preceding accession into this clinical trial.

The study is divided into 3 periods:
1. Screening Period: 1 week duration, assessment of eligibility.
2. Washout Period (1 week): Patients discontinue their current PEP, while remaining on all other allowed concomitant medication; specifically, patients are allowed to stay on medication for gastric acid control, including PPIs. At the end of the Washout Period, CFA is determined.
3. Treatment Period 1 (4 weeks): All patients receive their current PERT at an individual fix dose necessary to control steatorrhea.
4. Treatment Period 2 (4 weeks): Group 1 is randomized to receive 4 capsules per meal of Composition A at fixed Units/kg dose. Group 2 will be randomized to receive Composition B at fixed Units/kg dose. Group 3 is administered the same PERT given prior to screening for 4 weeks at the dose they are initially on. At the end of the Treatment Period 2, CFA is determined.
5. Frequency and severity of pain is recorded during Washout and the Treatment Periods on a daily basis.

Efficacy is assessed by comparing frequency and severity of pain as well as use of pain medication between Treatment Periods for each of the treatment groups. Efficacy is also assessed by comparing CFA derived from a defined diet and 3-day quantitative stool collection between Treatment Period 2 and Washout period for each of the treatment groups. Finally, frequency and severity of pain, and CFA are compared between groups in Treatment Period 2.

After treatment with Composition A and Composition B, both compositions are effective for treating pancreatic pain, and both compositions are effective for treating pancreatic exit chronic insufficiency. Composition B is more effective than Composition A for treating pancreatic pain.

Example 10

A randomized, double-blind, dose-response control, crossover study was carried out to evaluate the efficacy of compositions according to the present invention. After screening, eligible patients started the placebo baseline ambulatory phase (4 days). On day 5, they were hospitalized for 3 to 5 days, to undergo a "baseline" 72-hour Coefficient of Fat Absorption (CFA) determination under a controlled diet and using a stool marker to indicate the beginning and end of the controlled diet period, while they continued receiving placebo treatment. At the end of the placebo baseline phase, patients were randomized to a "high dose followed by a low dose" or to a "low dose followed by a high dose" EUR-1008 dose sequence and proceeded to the first crossover phase. Each crossover phase consisted of a stabilization period for 6 days at home, followed by a hospitalization of 3 to 5 days to undergo a 72-hour CFA determination using a controlled diet and using a stool marker to indicate the beginning and end of the controlled diet period.

The primary efficacy objective of the study was to evaluate the difference in Coefficient of Fat Absorption (CFA) of patients treated with high dose enterically coated pancreatin vs. low dose enterically coated pancreatin in the treatment of signs and symptoms and management of malabsorption in patients with EPI associated with diagnosed Chronic Pancreatitis.

Eligible patients started the placebo baseline ambulatory phase (4 days). On day 5, they were hospitalized for 3 to 5 days, to undergo a "baseline" 72-hour CFA determination under a controlled diet and using a stool marker to indicate the beginning and end of the controlled diet period, while they continued receiving placebo treatment. At the end of the placebo baseline phase, patients were randomized to a "high dose followed by a low dose" or to a "low dose followed by a high dose" enterically coated pancreatin dose sequence and proceeded to the first crossover phase. Each crossover phase consisted of a stabilization period for 6 days at home, followed by a hospitalization of 3 to 5 days to undergo a 72-hour CFA determination using a controlled diet and using a stool marker to indicate the beginning and end of the controlled diet period.

The high dose (7×20,000 USP Lipase Units capsules, Composition 4, Table 20) was administered at the fixed daily dosage of 7 capsules per full calendar day, distributed according to the size (estimated fat content) of the meals (possible example: 2 capsules with breakfast, 2 capsules with lunch, 2 capsules with dinner and 1 capsule with a snack).

TABLE 20

| | Content (mg/capsule) for each Dosage Strength | | | |
|---|---|---|---|---|
| Component | Composition 1 (µT) | Composition 2 (MT) | Composition 3 (MT) | Composition 4 (MT) |
| | µT or MT | | | |
| Pancrelipase | 55.7 (5,000 USP units) | 108.9 (10,000 USP units) | 163.4 (15,000 USP units) | 217.8 (20,000 USP units) |
| Croscarmellose Sodium | 1.9 | 3.6 | 5.5 | 7.3 |
| Hydrogenated Castor Oil | 0.6 | 1.2 | 1.8 | 2.4 |

TABLE 20-continued

| | Content (mg/capsule) for each Dosage Strength | | | |
|---|---|---|---|---|
| Component | Composition 1 (μT) | Composition 2 (MT) | Composition 3 (MT) | Composition 4 (MT) |
| Colloidal Silicon Dioxide | 0.3 | 0.6 | 0.9 | 1.2 |
| Cellulose Microcrystalline | 3.1 | 6.1 | 9.1 | 12.1 |
| Magnesium Stearate | 0.3 | 0.6 | 0.9 | 1.2 |
| Coating | | | | |
| Hypromellose Phthalate | 12.2 | 18.9 | 28.4 | 37.8 |
| Talc | 6.1 | 9.5 | 14.2 | 18.9 |
| Triethyl Citrate | 1.2 | 1.92 | 2.8 | 3.8 |

The low dose (7×5,000 USP Lipase Units capsules, Composition 1, Table 20) was administered at the fixed daily dosage of 7 capsules per full calendar day, distributed according to the size (estimated fat content) of the meals (possible example: 2 capsules with breakfast, 2 capsules with lunch, 2 capsules with dinner and 1 capsule with a snack).

Matched placebo was administered at the fixed daily dosage of 7 capsules per full calendar day, as for active treatment. Each crossover treatment phase consisted of a stabilization period for 6 days at home, followed by a hospitalization of 3 to 5 days.

The mean CFA was significantly higher following treatment with both dose levels than at the end of the placebo baseline period. The mean changes from the placebo baseline period were 7.19±14.49 (p<0.001) for the low dose and 8.18±17.35 (95% CI, 4.10 to 12.26) for the high dose. The difference between LS means of the high dose and low dose was 1.023% (95% CI, −0.656 to 2.701), thus showing the difference between doses was not statistically significant (p=0.228). Thus, this study surprisingly found that the low level of coated enzyme was effective in correcting fat malabsorption in patients with chronic pancreatitis and that higher doses do not lead to any increase in the coefficient of fat absorption (CFA).

These results show that substantially lower doses of enterically coated digestive enzymes are effective to treat pancreatic exocrine insufficiency than are conventionally used. For example, the FDA label for CREON® pancrelipase capsules states that enzyme dosing for adults "should begin with 500 lipase units/kg of body weight per meal for those older than age 4 years to a maximum of 2,500 lipase units/kg of body weight per meal". Thus, for a 70 kg adult, eating 3½ meals/day (i.e., 3 meals and 1 snack), the recommended daily dosage of CREON® pancrelipase would range from about 122,500 lipase units to about 612,500 lipase units. In contrast, the present study shows that daily dosages as low as 35,000 lipase units are effective in treating pancreatic exocrine insufficiency—less than 30% of the conventionally accepted minimum dose of digestive enzymes.

In addition, the results of this study also show that a small amount of coated enzyme may be used to correct for fat malabsorption, while a larger quantity of uncoated enzyme may be included in a single dosage form for the treatment of pancreatic pain. Such a product would not be an excessive increase in pill burden over current usage or a significant overall increase in the level of enzymes consumed, thus maintaining the safety characteristics of the drug whilst preserving its efficacy in treating malabsorption. Particularly, there would be sufficient uncoated protease immediately available on exiting the stomach to adequately degrade CCK-releasing peptide, and thus will be effective in treating two major symptoms of chronic pancreatitis; pain and malabsorption with a single medication. Accordingly, a dosage form containing both enterically coated and uncoated digestive enzymes in a single pill or capsule will be effective for the treatment of chronic pancreatitis and any pancreatic disease presenting with both pain and malabsorption.

The foregoing description of the invention has been presented for the purpose of illustration and description. It is not intended to be exhaustive or to limit the invention to the precise form disclosed. Modifications and variations are possible in light of the above teachings. The descriptions of the embodiments were chosen in order to explain and to describe the principles of the present invention and its practical application, and are not meant to be limiting on the scope of the claims.

All publications and patents or patent applications cited herein are incorporated by reference in their entirety to the same extent as if each individual publication, patent, or patent application were specifically and individually indicated incorporated by reference.

We claim:

1. A multi-particulate digestive enzyme composition consisting essentially of coated digestive enzyme-containing beads, and uncoated digestive enzyme-containing beads, wherein:
    the enterically coated digestive enzyme-containing beads comprise a core and an enteric coating disposed over the core, wherein the core comprises a therapeutically effective amount of digestive enzymes, and the enteric coating comprises an enteric polymer; and
    the uncoated digestive enzyme-containing beads comprise a therapeutically effective amount of digestive enzymes, and is substantially free of an enteric polymer coating; wherein
    the digestive enzymes comprise lipase and protease, and the ratio of lipase and protease activities in the enterically coated digestive enzyme-containing beads to the lipase and protease activities in the uncoated digestive enzyme-containing beads ranges from about 5:95 to about 50:50.

2. The multi-particulate digestive enzyme composition of claim 1, wherein the digestive enzymes comprise lipase and protease, and the ratio of lipase and protease activities in the enterically coated digestive enzyme-containing beads to the lipase and protease activities in the uncoated digestive enzyme-containing beads ranges from about 5:95 to about 25:75.

3. The multi-particulate digestive enzyme composition of claim 1, wherein the digestive enzymes comprise lipase and protease, and each of the enterically coated and uncoated digestive enzyme-containing beads have substantially the same protease and lipase activity.

4. A dosage form comprising the multi-particulate digestive enzyme composition of claim 1.

5. The dosage form of claim 4, wherein the enterically coated digestive enzyme-containing beads have a total lipase activity ranging from about 2000 USP lipase units to about 10,000 USP lipase units.

6. The dosage form of claim 4, wherein the enterically coated digestive enzyme-containing beads have a total protease activity ranging from about 6800 USP protease units to about 34,000 USP protease units.

7. The dosage form of claim 5, wherein the enterically coated digestive enzyme-containing beads have a total protease activity ranging from about 6800 USP protease units to about 34,000 USP protease units.

8. The dosage form of claim 4, wherein the uncoated digestive enzyme-containing beads have a total lipase activity ranging from about 10,000 USP lipase units to about 18,000 USP lipase units.

9. The dosage form of claim 4, wherein the uncoated digestive enzyme-containing beads have a total protease activity ranging from about 34,000 USP protease units to about 62,000 USP protease units.

10. The dosage form of claim 8, wherein the uncoated digestive enzyme-containing beads have a total protease activity ranging from about 34,000 USP protease units to about 62,000 USP protease units.

11. The dosage form of claim 4, wherein the enterically coated digestive enzyme-containing beads have a total lipase activity ranging from about 2000 USP lipase units to about 4,000 USP lipase units.

12. The dosage form of claim 4, wherein the enterically coated digestive enzyme-containing beads have a total protease activity ranging from about 6800 USP protease units to about 13,600 USP protease units.

13. The dosage form of claim 11, wherein the enterically coated digestive enzyme-containing beads have a total protease activity ranging from about 6800 USP protease units to about 13,600 USP protease units.

14. The dosage form of claim 4, wherein the uncoated digestive enzyme-containing beads have a total lipase activity ranging from about 14,000 USP lipase units to about 18,000 USP lipase units.

15. The dosage form of claim 4, wherein the uncoated digestive enzyme-containing beads have a total protease activity ranging from about 47,000 USP protease units to about 62,000 USP protease units.

16. The dosage form of claim 14, wherein the uncoated digestive enzyme-containing beads have a total protease activity ranging from about 47,000 USP protease units to about 62,000 USP protease units.

17. The dosage form of claim 4, in the form of a capsule filled with the multi-particulate digestive enzyme composition.

18. A method of treating pancreatitis pain, comprising administering the composition of claim 1 to a patient in need thereof.

19. A method of treating pancreatitis pain and pancreatic insufficiency, comprising administering the composition of claim 1 to a patient in need thereof.

20. The method of claim 19, wherein said administering comprises administering, per meal, an amount of multi-particulate digestive enzyme composition such that the lipase activity of the enterically coated digestive enzyme-containing beads ranges from about 8000 to about 40,000 USP lipase units, and the lipase activity of the uncoated digestive enzyme-containing beads ranges from about 40,000 to about 72,000 USP lipase units.

21. A method of treating pancreatic exocrine insufficiency, comprising administering to a patient in need thereof a therapeutically effective dose of an enterically coated digestive enzyme composition of claim 1, wherein said dose ranges from about 100 to about 300 USP lipase units/kg/meal.

22. The method of claim 21, wherein the daily dose of said enterically coated digestive enzyme ranges from about 35,000 to about 90,000 USP lipase units.

23. The method of claim 21, wherein said the enterically coated digestive enzyme is in the form of a capsule comprising enterically coated digestive enzyme-containing beads;
wherein the enterically coated digestive enzyme-containing beads comprise a core and an enteric coating disposed over the core, wherein the core comprises a therapeutically effective amount of one or more digestive enzymes, and the enteric coating comprises an enteric polymer.

* * * * *

UNITED STATES PATENT AND TRADEMARK OFFICE
CERTIFICATE OF CORRECTION

| | | |
|---|---|---|
| PATENT NO. | : 8,784,884 B2 | Page 1 of 1 |
| APPLICATION NO. | : 12/568064 | |
| DATED | : July 22, 2014 | |
| INVENTOR(S) | : Perrett et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 781 days.

Signed and Sealed this
Thirteenth Day of October, 2015

Michelle K. Lee
*Director of the United States Patent and Trademark Office*